United States Patent [19]

Wagner et al.

[11] 4,161,581

[45] Jul. 17, 1979

[54] POLY-[(DIALKYL AND HYDROXY-DIALKYL-IMINO)ETHYLENE HALIDES] AND PROCESS

[75] Inventors: Arthur F. Wagner, Princeton; Nathaniel Grier, Englewood; Tsung-Ying Shen, Westfield, all of N.J.

[73] Assignee: Merck & Co., Inc., Rahway, N.J.

[21] Appl. No.: 837,980

[22] Filed: Sep. 29, 1977

Related U.S. Application Data

[63] Continuation-in-part of Ser. No. 462,263, Apr. 19, 1974, abandoned, which is a continuation-in-part of Ser. No. 369,042, Jun. 11, 1973, abandoned.

[51] Int. Cl.$^2$ .............................................. C08G 73/02
[52] U.S. Cl. ........................... 525/411; 260/567.6 P; 424/78; 528/403; 528/423; 528/424; 525/414
[58] Field of Search ............ 260/2 R, 2 EN, 567.6 P; 528/404, 424, 423, 403

[56] References Cited

U.S. PATENT DOCUMENTS

| | | | |
|---|---|---|---|
| 2,884,057 | 4/1959 | Wilson et al. | 260/2 R |
| 3,372,129 | 3/1968 | Phillips | 260/2 R |
| 3,489,686 | 1/1970 | Parran | 260/2 EN |
| 3,575,797 | 4/1971 | Lahmann et al. | 260/2 R |
| 3,632,507 | 1/1972 | Witt | 260/2 R |

FOREIGN PATENT DOCUMENTS 396351 11/1974 U.S.S.R. ................... 260/2 EN

*Primary Examiner*—Wilbert J. Briggs, Sr.
*Attorney, Agent, or Firm*—Walter Patton; Harry E. Westlake, Jr.

[57] ABSTRACT

Novel polymers having a linear backbone which is free from both branching and cross-linking, comprising either tertiary or quaternized nitrogen atoms linked to each other through ethylene groups. These polymers are useful as antimicrobials, flocculating agents, antistatic agents, electroconductive agents for coating paper, chelating agents and bile acid binding agents, as well as in similar applications where their high charge to weight ratio and fully accessible nitrogen atoms can be employed. The polymers are obtained by the polymerization of an oxazoline, hydrolysis or direct reduction, nitrogen substitution, and optional quaternization of the resulting polymer.

4 Claims, No Drawings

POLY-[(DIALKYL AND HYDROXY-DIALKYL-IMINO)ETHYLENE HALIDES] AND PROCESS

This is a continuation-in-part of application Ser. No. 462,263, filed Apr. 19, 1974 which, in turn, is a continuation-in-part of application Ser. No. 369,042, filed June 11, 1973, both now abandoned.

DISCLOSURE OF THE INVENTION

This invention relates to novel polymers, together with methods for their preparation. More particularly, this invention relates to polymers derived from oxazolines which have a linear backbone free from both branching and crosslinking, comprising either tertiary or quaternized nitrogen atoms linked to each other through ethylene groups.

These polymers are advantageously employed as antimicrobials, flocculating agents, electroconductive agents in paper coatings, antistatic agents, chelating agents, and bile acid binding agents, as well as in similar applications where their high charge to weight ratio, and the accessibility of their charged nitrogen can advantageously be employed.

They are active as nonabsorbable gastrointestinal bile acid binding agents, which binding is known to reduce levels of blood serum cholesterol. The incidence of higher than normal blood serum cholesterol levels in humans is apparently associated with atherosclerosis and other hypercholesteremic disease signs, which can result in occlusion of the circulation, giving rise to coronary, cerebrovascular, and some forms of peripheral vascular diseases.

Heretofore, a variety of bile acid binding agents have been employed. These include iron salts which produce insoluble precipitates with bile acids, organic bases to act similarly, and polymers having a salt-forming capability. Readily absorbable precipitants present acute and chronic toxicity hazards. The use of non-absorbable polymers to avoid such toxicity problems has not provided a suitable alternative, because the average effective adult daily dose of such polymers heretofore employed ranges up to 40 grams. The physical bulk of such a dose, especially when of a water-insoluble cross-linked resin, can induce partial blockage of the gastrointestinal tract and an unpleasant, heavy sensation. Furthermore, any objectionable odor and taste of so large a dose is difficult to mask. There has therefore been only limited benefit derived from treatment using these prior bile acid binding agents, although the incidence of disease linked to hypercholesteremia is extremely high and continues to rise alarmingly.

We have now found that the novel linear, unbranched polymers hereinafter described are exceptionally effective in binding or sequestering bile acids in the gastrointestinal tract, and in lowering blood serum levels of cholesterol. That the polymers of this invention are linear and unbranched is critical to the advance made by this invention. Thus, while some references, e.g., U.S. Pat. No. 3,308,020 disclose monomer units that are similar to the monomer units herein disclosed, these prior art polymers, by virtue of the materials and methods used to prepare them, are highly branched; both Gibbs et al, *Journal of American Chemical Society*, 57 1137 (1935), and Noguchi et al, *Macromolecules*, 5, 261 (1972), assert that attempts to polymerize dimethylaminoethylene halides yield only cyclic dimers, notwithstanding the disclosures contained in German Pat. Nos. 1,131,694 and 1,126,396.

The polymers of this invention are represented by the following Formula I:

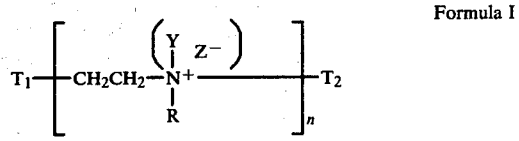

Formula I wherein m is 0 or 1; n is an integer such that the number average molecular weight is from 300–50,000; $Z^-$ is a monovalent or polyvalent counter anion; $T_1$ and $T_2$ are terminal groups; R is loweralkyl, such as methyl or ethyl; and Y is hydrogen, loweralkyl, such as methyl or ethyl, monohydroxy-substituted $C_1$ to $C_4$ alkyl, such as 2-hydroxyethyl, ammonioloweralkyl, such as ammoniopropyl, loweralkylammonioloweralkyl, such as methylammoniopropyl, diloweralkylammonioloweralkyl, such as dimethylammonioethyl, or triloweralkylammonioloweralkyl, such as trimethylammonioethyl.

As used herein, "lower alkyl" stands for alkyl containing from 1 to 4 carbon atoms; the term "salt forming nitrogen" means a nitrogen atom (i.e., an imino group or a substituted imino group) sufficiently basic that it is either present as a quaternary or acid addition salt, or can form such salt with acids; the term "linear polymer backbone" refers to a polymer having only acyclic groups, i.e., ethylene, linking the nitrogen atoms in a single continuous chain; the term "unbranched" means a polymer having no repeating monomer units extending from the polymer backbone; and the term "crosslinked" denotes a joining of two linear backbones.

The exact nature or identity of the terminal groups $T_1$ and $T_2$ is immaterial to the invention, or to the utility of the presently invented polymers, since the large number of monomer components in the polymer chain are necessarily the major determinants of the chemical and physical propererties of the polymer. However, in the polymers prepared as hereinafter described, and depending on the solvent used to effect recovery of product from the oxazoline polymerization, the structures of the terminal groups are ordinarily, for $T_1$, $(R)_2N$— when m is 0, and $(R)_2YN^+(Z^-)$— when m is 1; and for $T_2$, —$CH_2CH_2$—W, where W is hydroxy or loweralkoxy such as methoxy or ethoxy, and R and Y have the meanings hereinabove defined.

Throughout this description, $Z^-$ represents an anion which counters the charge on the quaternized or protonated imino group, and thus can be a monovalent anion. It is to be understood, however, that $Z^-$ is contemplated to include polyvalent anions where one anion can counter the charge on more than one charged imino group. Thus, $Z^-$ can include anions of inorganic acids, as well as from organic acids such as, for example, halide, e.g., chloride, bromide, or iodide; sulfate; bisulfate; phosphate; acetate; ascorbate; citrate; hydroxycitrate; carbonate; bicarbonate; nicotinate; glycinate; taurinate; salicylate; and other anions derived from physiologically non-toxic acids, especially salts of physiologically active acids such as those derived from clofibrate and halofenate, i.e., 2-(p-chlorophenoxy)-2-methylpropionic and 3-trifluoromethylphenoxy-(4-chlorophenyl) acetic acids. When such anions of physiologically active compounds are used to neutralize quaternized or protonated imino groups, it is apparent that only a portion of the charged imino groups may be so neutralized. The proportion of anion from the physiologically active compound is adjusted so that the amount administered with the polymer dosage falls within the desired range for the physiologically active compound.

The polymers of this invention are obtained through a sequence of steps, the first of which is the polymerization of the $\Delta^2$-oxazoline of the following Formula II:

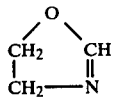

Formula II

This polymerization of the $\Delta^2$-oxazoline is known and is reported in *Polymer Journal*, 3, 35 (1972). We have found, however, that a more reliable polymerization is obtained by using trifluoromethylsulfonic acid in place of the initiators reported in the literature. Generally, from 0.005 to 0.1 moles of trifluoromethylsulfonic acid is used for each mole of a $\Delta^2$-oxazoline, with 0.01 mole of the trifluoromethylsulfonic acid per mole of $\Delta^2$-oxazoline being preferred. The polymerization of the $\Delta^2$-oxazoline is ordinarily carried out in a closed system in an inert solvent under substantially anhydrous conditions in an inert atmosphere such as nitrogen, at a pressure of from 1–100 atmospheres, and at a temperature of about 30° C. to 120° C. for a period of about 1–12 hours. By inert solvent, it is meant here and elsewhere in this specification, a solvent which is not reactive under these conditions either with reactants, products, or itself; dimethylformamide is the preferred solvent. After reaction is complete, which is readily ascertained by disappearance of the —C≡N— double bond in the infrared spectrum, the polymerization reaction mixture is admixed with a solvent preferably a dialkyl ether such as diethyl ether and the insoluble poly-[(formimino)ethylene] is recovered from the mixture by filtration, washed with dialkyl ether and dried. If desired, the polymerization reaction mixture is diluted with a lower alkanol such as methanol, the volatile components are then evaporated from the resulting alcoholic mixture under reduced pressure, and the resulting polymer is then purified by precipitation from a mixture of methanol-ether.

The poly-[(formimino)ethylene], prepared as described hereinabove, is heated with a mixture of more than one equivalent each of formaldehyde and formic acid, the reductive methylation mixture is treated with an excess of aqueous mineral acid, such as concentrated aqueous hydrochloric acid, and the resulting mixture is evaporated to dryness under reduced pressure to give poly-[(methylimino)ethylene salt] having the following Formula III:

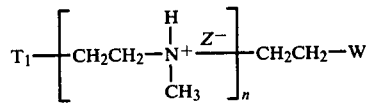

Formula III wherein n has the meaning hereinabove defined; $Z^-$ is the anion corresponding to the aqueous mineral acid (e.g. $Cl^-$) employed to treat the reductive methylation mixture; $T_1$ is $(CH_3)_2NHZ^-$; and W is alkoxy (e.g. methoxy) when the poly[(formimino)ethylene] polymer is recovered by diluting the polymerization reaction mixture with a lower alkanol (e.g. methanol) and the volatile components evaporated from the resulting alkanoic mixture, and is hydroxy when the said poly[(formimino)ethylene] polymer is recovered from the $\Delta^2$-oxazoline polymerization reaction mixture in the absence of an alkanol, as by the addition of diethyl ether. It will be noted that this poly[(methylimino)ethylene salt] of Formula III is also represented by Formula I on page 4 hereinabove where m is 1; $T_1$ is $(CH_3)_2NH^+Z^-$; $T_2$ is hydroxyethyl or lower alkoxyethyl; R is methyl; and Y is hydrogen.

This reductive methylation procedure is ordinarily conducted by adding the poly-[(formimino)ethylene] to a mixture of 97% to 100% formic acid and preferably 38% aqueous formaldehyde, and heating the resulting mixture to a temperature of from 30° C. to 100° C. for a period of from 20 to 100 hours. Although higher reaction temperatures may be used, such are not ordinarily employed in view of the increased rate of thermal decomposition of formic acid and the risk of degradation of the polymer. The polymerization reaction mixture is then treated with an aqueous mineral acid, preferably hydrochloric acid, and the excess formic acid, formaldehyde and mineral acid are evaporated under reduced pressure.

This poly[(methylimino)ethylene salt] or other poly[(loweralkylimino)ethylene salt], which has been isolated from the reduction mixture using diethylether or methanol, is reacted, in the form of its free base, with a quaternizing agent, preferably a lower alkyl (or substituted alkyl) halide YX, thereby forming the corresponding poly[(loweralkyl, Y-imino) ethylene halide] polymer. Thus, where the quaternizing agent is methyl chloride, the quaternized polymer is poly[dimethylimino)ethylene chloride]; when the quaternizing group is 2-bromoethyl-trimethylammonium bromide, the quaternized polymer is poly[{methyl-(2-trimethylammonioethyl)imino} ethylene dibromide]. These quaternary polyethyleneimine polymers, where poly[(loweralkylimino)ethylene] is used as starting material, are represented by Formula I on page 4 hereinabove where m is 1; R is loweralkyl; $Z^-$ is halide; $T_1$ is $(R)_2YN^+Z^-$—; and $T_2$ is hydroxy (or loweralkoxy)ethyl; and Y has the meaning designated on page 4. The quaternized polymer, poly[(dimethylimino)ethylene chloride], is represented by Formula I when m is 1; Y is methyl; R is methyl; $Z^-$ is chloride: $T_1$ is trimethylammonio chloride; and $T_2$ is hydroxy (or methoxy) ethyl. The quaternized polymer, poly[{methyl-(2-trimethylammonio ethyl)imino} ethylene dibromide], is represented by Formula I when m is 1; Y is 2-trimethylammonioethyl; R is methyl; $Z^-$ is dibromide; $T_1$ is N-(2-trimethylammonioethyl)N,N-dimethylammonio dibromide; and $T_2$ is 2-hydroxy (or 2-methoxy) ethyl.

In carrying out this quaternization reaction, the poly-[loweralkylimino)ethylene), which is usually obtained as the acid addition salt (Formula I where m is 1 and Y is hydrogen), is converted to the free base form (m=0) on treatment with an equivalent amount of base. At this stage, it is convenient, though not necessary to remove any inorganic salts by ultrafiltration techniques. This has the added advantage of also eliminating any other undesirable lower molecular weight material. The aqueous solution of the tertiary amine polymer is then evaporated under reduced pressure, and the residual product is dried prior to the quaternization reaction (when that reaction is conducted in non-aqueous solvent). The quaternization reaction is, however, not only conducted in inert non-aqueous solvents such as alcohols, ketones or dimethylformamide, preferably methanol, acetone or dimethylformamide, but is often advantageously carried out in aqueous solution, such as water alone, or mixtures of water-methanol, water-acetone or water-dimethylformamide. The quaternizing agents are usually halogen containing compounds, preferably bromo compounds. Other alkylating agents such as toluenesulfonate esters or trichloromethylsulfonate esters can also be employed. An excess of the alkylating agent YX is ordinarily employed; the YX may be a simple alkyl halide or the alkyl radical may also carry other functional groups which do not interfere with the quaternization reaction. A simple but by no means exhaustive list of acceptable quaternization reagents includes haloalkyl acid esters, haloalkyl acid amides, haloketones, 3-bromo-1-chloropropane, alkyl halohydrins, aralkyl halides, mono, di and tri-loweralkyl-substituted ammonioalkyl halides, alkoxyalkyl halides, alkylthioalkyl halides, allyl halides, and propargyl bromide.

The reaction is conducted by allowing a solution of the poly-[(loweralkylimino)ethylene] and alkylating agent YX in acetone, water, methanol, dimethylformamide, or mixtures thereof, to stand at 25° C. to 100° C. for three hours to several days depending on the temperature employed and the reactivity of the alkylating agent. The quaternization product thus formed, the poly-[(loweralkyl, Y-imino)ethylene halide], when insoluble in the reaction mixture, is conveniently isolated directly by filtration; in some instances, it is expedient to dilute the reaction mixture with several volumes of a non-solvent for the polymer prior to isolation; when the polymer is soluble in the reaction mixture, the volatile components may be evaporated under reduced pressure to give the polymer as a residual solid. The polymer is usually partially dried, ground to a powder and then dried under reduced pressure at temperatures of from 25° C. to 60° C.

When the poly-[(loweralkyl, Y-imino)ethylene halide] is prepared by the techniques of the prior steps, the anion $Z^-$ of the polymer is generally halide. The full range of polymers of formula I where the anion $Z^-$ differs from halide can be obtained by dissolving the formula I polymer, having a halide anion, in water, alcohol, or mixtures thereof in any proportion and passing the solution through a bed of anion exchange resin, either a synthetic or a zeolite type, where the halide ion is exchanged and replaced by the desired $Z^-$. The anion-exchange method employing a resin technique can be direct, that is, exchanging halide ion for $Z^-$ or one can first exchange halide ion for $OH^-$ and then, either by subsequent ion exchange or simple neutralization, exchange $OH^-$ for $Z^-$.

Additionally, chemical exchange techniques can be employed when a precipitate of a metal halide is less soluble than the added metal salt MZ. The precipitated metal halide can then be filtered from the solution of polymer.

A simple example of the latter technique involves treating a solution of poly-[(loweralkyl, Y-imino)ethylene bromide], i.e. containing the bromide counter anion, with an excess of freshly precipitated silver chloride. After the halide anion exchange is complete, the mixture of silver chloride and silver bromide is removed by filtration leaving a solution of the polymer containing the chloride counter anion, i.e. poly-[(loweralkyl-Y-imino)ethylene chloride]. Alternatively, the polymer where $Z^-$ is sulfate can be treated with solutions of water soluble calcium or barium salts. Thus, sulfate can be replaced with nitrate and the precipitate of barium sulfate removed.

Throughout this description, $Z^-$ represents an anion which counters the charge on the quaternized imino group, and thus can be a monovalent anion. It is to be understood, however, that $Z^-$ is contemplated to include polyvalent anions where one anion can counter the charge on more than one charged imino group. Thus, $Z^-$ can include anions of inorganic acids, as well as of organic acids such as, for example, halide, e.g., chloride, bromide, or iodide; sulfate; bisulfate; phosphate; acetate; ascorbate; citrate; hydroxycitrate; carbonate; bicarbonate; nicotinate; glycinate; taurinate; salicylate; and other anions derived from physiologically non-toxic acids, especially salts of physiologically active acids such as those derived from clofibrate and halofenate, i.e., 2-(p-chlorophenoxy)-2-methylpropionic and 3-trifluoromethylphenoxy-(4-chlorophenyl)acetic acids. When such anions of physiologically active compounds are used to neutralize quaternized imino groups, it is apparent that only a portion of the charged imino groups may be so neutralized. The amount of anion from the physiologically active compound is apportioned in a ratio such that the amount administered with the polymer dosage can fall within the desired range for the physiologically active compound.

Effective lowering of cholesterol blood levels is obtained by the oral administration of remarkably small dosages of the polymers of this invention. This enables a flexibility of formulation previously unavailable. The polymers can be finely divided powders and suitably used as such or preferably admixed with varying amounts of solid carrier agents such as colloidal silica, starches, sucrose, talc, lactose, cellulose; or modified cellulose, dry milk powder, protein powders such as soy flour, and the like. These are preferably made into unit dosage forms such as tablets, filled gelatin capsules or a foil or paper envelope containing the premeasured dose which can include supplementary vitamins and minerals, and which can be readily torn open and added to edible liquids such as fruit juices or other beverages. The unit dose composition may comprise from 10% to 99% by weight of polymer, the remainder being carriers, flavorings, excipients, flow agents and the like. In such a unit dose, the active polymer may comprise from 0.1 gm. to up to 10 gms. in powder packets.

Also suitable are aqueous solutions or suspensions which can be prepared and are preferably sweetened or flavored. Although not entirely desirable, the polymers can be mixed in various vehicles such as safflower or corn oil for oral ingestion as such or as an aqueous emulsion. These may also be encapsulated.

The total daily dosage of bile acid binding polymer is preferably divided into three or four equal portions and taken before each meal and prior to bedtime. This regimen provides for maximum resin contact time during periods of highest intestinal bile acid concentrations.

The polymers of this invention may be used alone, or, if desired, can be compounded together with triglyceride synthesis inhibitors or other bile acid binding agents for particular treatments. In addition, as heretofore stated, the polymers described herein form salts with the acids of clofibrate and halofenate, which salts are useful in cardiovascular disease therapy. The following examples are illustrative of the dosage forms which can be employed in the practice of our invention. Those skilled in the art of pharmaceutical compounding will be aware of variations which can be practical without departing from the spirit of our invention. It is anticipated that multiple dosages, e.g., two or three tablets or capsules can be taken at one time if higher dosages are prescribed.

Additional ingredients which may comprise the carrier portion of the compositions of this invention, can also have pharmacological activity and can include other choleretic agents such as tocamphyl florantyrone; taurine; and glycine; hypocholesteremic agents such as nicotinic acid; the D-isomer of 3,3',5-triiodothyronine; thyroxine-like compounds such as sodium L-thyroxin and sodium D-thyroxine; triiodothyropropionic acid; nafoxidine hydrochloride, 5-methylpyrazole-3-carboxylic acid and 3-methyl-5-isoxazolecarboxylic acid; fecal softeners such as poloxalkol and dioctyl sodium sulfosuccinate; as well as unsaturated fatty acids such as linoleic acid, arachidonic acid and linolenic acid. Although not preferred, edible vegetable oils such as corn oil and safflower oil are also suitable.

POWDER PACKETS

Linear, unbranched and non-cross-linked poly[{methyl-(2-trimethylammonioethyl)imino}ethylene dichloride] is finely powdered and blended with 1% by weight of lactose powder. Aluminum envelopes containing a paper bag liner are individually filled with 0.55 g. of the mixture and sealed against moisture to prevent caking.

HARD GELATIN CAPSULES

A 250 mg. dose of poly-[{methyl-(2-trimethylammonioethyl)imino}ethylene dichloride] containing 1% by weight of lactose as described above is filled into the appropriate size hard gelatin capsules.

Alternatively, a dry filled capsule can be prepared from the following components:

| | |
|---|---|
| poly-[{methyl-2-trimethylammonioethyl)imino}-ethylene dichloride] | 300 mg. |
| corn starch | 150 mg. |
| cab-o-sil (anhydrous silica) | 5 mg. |

If capsules of lower potency are to be prepared, the capsule size can be decreased or additional corn starch or other diluent employed. When using smaller amounts of active ingredient it is anticipated that a multiple capsule dose can be administered.

COMPRESSED TABLETS

A dry blend is prepared with the following components:

| | |
|---|---|
| poly-[{(methyl-(2-trimethylammonioethyl)imino}-ethylene dichloride] | 1 kg. |
| sucrose, powdered | 30 gms. |
| collidal silica | 10 gms. |
| carbowax-4000 | 30 gms. |

Four thousand tablets are pressed therefrom by direct compression each of which tablets contains 250 mg. of the ionene polymer.

Likewise, compressed tablets are prepared such that each tablet contains:

| | |
|---|---|
| poly-[{(methyl-(2-trimethylammonioethyl)imino}-ethylene dichloride] | 300 mg. |
| corn starch | 30 mg. |

-continued

| | |
|---|---|
| polyvinylpyrrolidone | 10 mg. |
| magnesium stearate | 3 mg. |

After tableting, a plastic film can be applied to the tablets to seal them from moisture in ways well known in the art.

In addition, an enteric coating may be applied, if desired. Such a coating may comprise fats, fatty acids, waxes and mixtures thereof, shellac, ammoniated shellac, and cellulose acid phthalates applied by techniques well known and accepted.

In place of the poly-[{(methyl-2-trimethylammonioethyl)imino}ethylene dichloride], there may be substituted the other polymer salts of our invention.

Other binding agents may be used in place of sucrose, such as dextrose, lactose, methyl cellulose, natural and synthetic gums, and the like. Talc can replace the calcium or magnesium stearate. A variety of readily available non-toxic anti-caking agents may be substituted for the colloidal silica.

Other lubricants, diluents, binders, coloring agents, flavoring agents and disintegrators can be used as are known in the art employing wet or dry granulation techniques, direct compression, spray drying, and the like.

If desired, a chewable tablet can be prepared from preferably microencapsulated polymer particles by dry granulation as follows:

| | |
|---|---|
| microencapsulated poly-[{(methyl-2-trimethyl-ammonioethyl)imino}ethylene dichloride] | 750 mg. |
| mannitol | 300 mg. |
| sodium saccharine (or other sweetener) | 2 mg. |
| oil of peppermint | 1 mg. |
| carbowaz-4000 | 15 mg. |
| microcrystalline cellulose | 100 mg. |

All of the above dosage forms are administered orally in an effective bile acid binding dose. For lowering blood serum cholesterol levels, generally a single or multiple dose of from about 0.1 to 5.0 grams is suitable although doses in excess of 10 grams can be given where indicated. Such doses are also effective in relieving symptoms of biliary pruritus. Administration can be in a variety of forms, such as a suspension, in an aqueous solution, as a chewable or a coated tablet, or in a capsule, and can be continued for an extended course of treatment. Generally, medication is on a daily basis with each day's dose taken in divided portions, preferably with meals.

For control of hypercholesterolemia, the particular individual dosage, given variances in metabolism and diet, is preferably arrived at through an initial determination and continued monitoring of blood serum cholesterol levels. Thus, a moderate dosage might be employed initially, and increased until the desired blood serum cholesterol level is achieved and maintained. For an initial dose, pending such individual adjustment, from 2.5 to 100 mg./kg. of body weight per day is satisfactory.

The following examples illustrate methods of carrying out the present invention, but it is to be understood that these examples are given for purposes of illustration and not of limitation.

EXAMPLE 1

Poly-[(Methylimino)ethylene]

A mixture of 25 g. of poly-(formiminoethylene), prepared as described hereinbelow, 504 g. of 97%–100% formic acid and 118 g. of 38% aqueous formaldehyde (formalin) is heated at 100° C. for 60 hours. The reaction mixture is cooled, 210 ml. of concentrated hydrochloric acid is added, and the mixture is concentrated to dryness under reduced pressure at 50° C. After the product is washed with methanol, then ether, and dried, 34.6 g. of poly-[(methylimino)ethylene hydrochloride] is obtained. A solution containing 0.325 mole of sodium hydroxide is prepared by dissolving 17.55 g. of sodium methoxide in 400 ml. of water. To this is added 28.6 g. (0.31 mole) of poly-[(methylimino)ethylene hydrochloride], and the total volume of the solution is made up to 500 ml. by the addition of water. The solution is then desalted and also rid of any product with a molecular weight of less than 1000 using an Amicon filter cell equipped with a UM2 Diaflo Ultrafilter. Next, the solution is concentrated under reduced pressure at 50° C. yielding 16 g. of poly-[(methylimino)ethylene].

EXAMPLE 2

Poly-[(Dimethylimino)ethylene Chloride]

Five hundred milligrams (5.4 milliequiv.) of poly[(methylimino)ethylene hydrochloride] is dissolved in 50 ml. of methanol containing 291 mg. (5.4 mmoles) of sodium methoxide. The solution is cooled in an acetone-dry ice bath, and 10 g. of methyl chloride is condensed into the solution. This mixture is heated in a sealed tube at 80° C. for five hours. This mixture is concentrated to dryness under reduced pressure and the product is taken up in 3 ml. of anhydrous methanol and filtered and the solution is concentrated to dryness. Dissolution of the product in methanol, filtration, and then concentration to dryness is repeated several times. The filtrate is concentrated under reduced pressure yielding 400 mg. of poly-[(dimethylimino)ethylene chloride].

EXAMPLE 3

Poly-[(Dimethylimino)ethylene Bromide]

A solution of 860 mg. (20 milliequiv.) of poly-(iminoethylene) in 30 ml. of methanol is treated with 9.5 g. (100 mmoles) of methyl bromide at 50° C. for three hours. The reaction mixture is concentrated to dryness under reduced pressure. The residue is treated with 1.08 g. (20 mmoles) of sodium methoxide in 10 ml. of methanol and concentrated to dryness. The residue is taken up in 30 ml. of anhydrous methanol and treated with 9.5 g. (100 mmoles) of methyl bromide; the solution is heated at 50° C. for three hours. After concentration, the product is taken up in water, and the solution is subjected to ultrafiltration through a UM 2 Diaflo Ultrafilter. The retentate is then concentrated under reduced pressure yielding 2.8 g. of poly-[(dimethylimino)ethylene bromide].

EXAMPLE 4

Poly-[(Dimethylimino)ethylene Methosulfate]

0.5 Grams of poly-[(methylimino)ethylene hydrochloride] is dissolved in 50 ml. of methanol containing 0.29 g. of sodium methoxide. The solution is concentrated to about 20 ml. and 0.7 g. of dimethyl sulfate is added. The solution is then heated 6 hours at 50° C., and the product is precipitated by pouring the solution into a large volume of acetone or by evaporation of the methanol followed by acetone wash. The product is dried at ambient temperature under reduced pressure.

EXAMPLE 5

Poly-[{(2-Hydroxyethyl)methylimino}ethylene Chloride]

The procedure of Example 2 is followed, but there is used 15.8 g. of ethylene chlorohydrin in place of the 10 g. of methyl chloride. The mixture is heated at 80° C. for five to seven hours and then freed of solvents and excess reagents by stripping under reduced pressure. The residue is poly-[{(2-hydroxyethyl)methylimino}ethylene chloride].

In an analogous manner an equivalent amount of propylene chlorohydrin or sec-propylene chlorohydrin is respectively substituted for the ethylene chlorohydrin giving poly-[{(1-methyl-2-hydroxyethyl)methylimino}ethylene chloride] and poly-[{(2-hydroxypropyl)methylimino}ethylene chloride].

EXAMPLE 6

Poly-[(2-Hydroxyethylimino)ethylene]

0.5 Grams of the poly-(iminoethylene) is dissolved in 50 ml. of methanol and heated with 0.35 g. ethylene oxide in a sealed tube under nitrogen at 60° C. for three hours. The solvent and excess epoxide are removed by stripping under reduced pressure. The residue is poly-[(2-hydroxyethylimino)ethylene].

EXAMPLE 7

Poly-[{(2-Hydroxybutyl)-2-hydroxyethylimino}ethylene Bromide]

The poly-[(2-hydroxyethylimino)ethylene] from Example 6 is heated in 50 ml. of acetone with 20 g. of 2-hydroxybutyl bromide at 80° C. to 90° C. in a sealed tube for six to eight hours.

The product is recovered as before by removal of solvent and excess reagent under reduced pressure. The residue is poly-[{(2-hydroxybutyl)-2-hydroxyethylimino} ethylene bromide].

EXAMPLE 8

Poly-[(Dimethylimino)ethylene Bromide]

A solution of 21.7 g. (0.38 equiv.) of poly-[(methylimino)ethylene] in 130 ml. of anhydrous methanol is cooled and 364 g. (3.8 moles) of condensed methyl bromide is added. The mixture is a glass-lined pressure reactor is heated at 50° C. for five hours. After the mixture is cooled, the product is isolated by filtration, washed with ether and dried under reduced pressure to give 58 g. of poly-[(dimethylimino)ethylene bromide].

EXAMPLE 9

Poly-[(Dimethylimino)ethylene Chloride]

A solution of 58 g. of poly-[(dimethylimino)ethylene bromide] (0.38 mole) in three liters of water is passed slowly (10 ml./min.) through a 770 ml. column of 200–400 mesh AG1-X8 quaternary ammonium chloride resin (1078 milliequivalents of Cl−). After 4200 ml. of effluent is collected, it is concentrated under reduced pressure at 50° C.–55° C. and dried to give about 37 g. of poly-[(dimethylimino)ethylene chloride].

EXAMPLE 10

Poly-[(Dimethylimino)ethylene Ascorbate]

5.0 Grams of poly-[(dimethylimino)ethylene chloride] is dissolved in 75 ml. of distilled water and passed down a column containing 100 grams (0.5 mole Cl− exchange capacity) of a polystyrene resin, the benzene ring of which is substituted with 4-methotrimethyl ammonium hydroxide (Bio Rad Ag 1×8). Six column volumes of the eluate (450 ml.) containing poly-[(dimethylimino)ethylene hydroxide] is collected, concentrated to 150 ml., cooled to 15° C., and neutralized with 8.8 gms. (0.05 moles) of ascorbic acid, U.S.P. The clear neutralized solution is then shell frozen and lyophilized to give a white solid which is readily pulverized.

EXAMPLE 11

Poly-[{Methyl-(2-trimethylammonioethyl)}imino ethylene Dibromide]

A solution of 570 mg. (10 milliequiv.) of poly-[(methylimino)ethylene] and 9.9 g. (40 mmoles) of 2-bromoethyltrimethylammonium bromide in 40 ml. of dimethylformamide is heated at 75° C. for 12 hours. After being cooled, the reaction mixture is diluted with five volumes of ether, and the precipitated material is recovered by filtration, and dried under reduced pressure to give poly-[{methyl-(2-trimethylammonioethyl)imino}ethylene dibromide].

The poly-(iminoethylene), poly-[(formimino)ethylene], and poly-[(methylimino)ethylene] and its hydrochloride, utilized as starting materials in above examples may be prepared as follows. A solution of 44 g. of $\Delta^2$-oxazoline and 870 mg. of freshly distilled boron trifluoride etherate in 175 ml. of purified dimethylformamide is placed in a pressure reactor containing a glass liner and the system is purged with nitrogen. The mixture is heated at 80° C. for five hours and then diluted with methanol and filtered yielding 30 g. of the poly-[(formimino)ethylene] polymer. In a five-hour reaction period at 80° C. and boron trifluoride etherate catalyst at 0.01 mole ratio to that of $\Delta^2$-oxazoline, the yield of solid polymer ranges from 13.2% to at least 68%.

Alternatively, a solution of 217 g. (3.06 moles) of $\Delta^2$-oxazoline and 4.6 g. (0.03 moles) of trifluoromethylsulfonic acid in 800 ml. of purified dimethylformamide in a sealed tube and under a nitrogen atmosphere is heated at 90° C. and agitated for five hours. After being cooled, the mixture is diluted with 1200 ml. of anhydrous methanol and the product is isolated by filtration. The product is washed with methanol and then ether prior to being dried under reduced pressure. This reaction yields 150 g. of poly-[(formimino) ethylene].

A solution of 3 g. of poly-[(formimino)ethylene] and 3 g. of sodium hydroxide in 35 ml. of water is heated with stirring at 98° C. for three hours. The solution is cooled to room temperature and the white solid which precipitates is isolated by filtration washed thoroughly with water and dried in vacuo, yielding 1.6 g. of poly-(iminoethylene).

Two and five-tenths grams of poly-(iminoethylene) is added slowly to 12 g. of 90% formic acid and 5.5 g. of 38% aqueous formaldehyde is added. After the mixture is heated at 100° C. for 72 hours, it is cooled, and 5.5 ml. of concentrated HCl is added. The mixture is concentrated to dryness under reduced pressure, yielding 5 g. of poly-[(methylimino)ethylene hydrochloride].

Various changes and modifications may be made in carrying out the present invention, without departing from the spirit and scope thereof. Insofar as these changes and modifications are within the purview of the annexed claims, they are to be considered as part of this invention.

What is claimed is:

1. A method of preparing a linear unbranched non-cross-linked polymer comprising repeating units of the formula

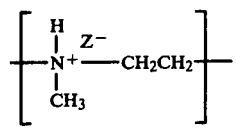

where Z− is a counteranion, which comprises admixing a polymer comprising repeating units of the formula

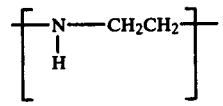

with an excess of aqueous formaldehyde and formic acid, and heating the resulting admixture to a temperature of from 30° to 100° C. for up to 100 hours wherein a mixture of 97 to 100% formic acid and aqueous formaldehyde is employed and, following the heating of said admixture, there is then added to the reaction mixture an aqueous mineral acid HZ, and the aqueous acidic mixture is subjected to distillation under reduced pressure thereby removing reagents and by-products.

2. A method of preparing a linear, unbranched, non-cross-linked polymer comprising repeating units of the formula

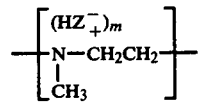

where m is the integer 1 or 0, and Z− is a counter anion, which comprises reacting a polymer comprising repeating units of the formula

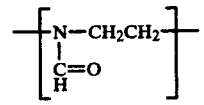

with an excess of a chemical reductant.

3. A method according to claim 2 where m is the integer 1, which comprises admixing a polymer comprising repeating units of the formula

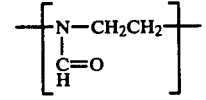

with an excess of formaldehyde and formic acid, and heating the resulting admixture at a temperature of from 30° to 100° C. for up to 100 hours.

4. A method according to claim 3 where a mixture of 97 to 100% formic acid and aqueous formaldehyde is employed and, following the heating of said admixture, there is then added to the reaction mixture an aqueous mineral acid HZ, and the aqueous acidic mixture is subjected to distillation under reduced pressure thereby removing reagents and by-products.

* * * * *

UNITED STATES PATENT AND TRADEMARK OFFICE
CERTIFICATE OF CORRECTION

PATENT NO. : 4,161,581
DATED : July 17, 1979
INVENTOR(S) : W Arthur F. Wagner et al.

It is certified that error appears in the above-identified patent and that said Letters Patent are hereby corrected as shown below:

Column 2, structural formula I, should appear as shown below.

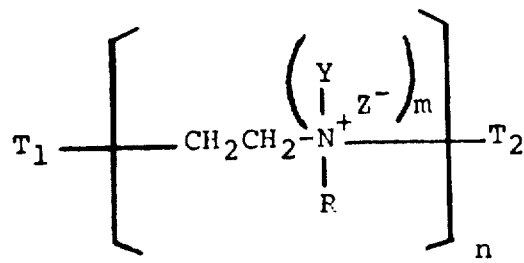

Signed and Sealed this

Thirtieth Day of October 1979

[SEAL]

Attest:

RUTH C. MASON
*Attesting Officer*

LUTRELLE F. PARKER
*Acting Commissioner of Patents and Trademarks*